(12) United States Patent
Wysocki et al.

(10) Patent No.: US 9,186,070 B2
(45) Date of Patent: Nov. 17, 2015

(54) APPARATUS FOR ASSESSING THE STRESS ON THE CIRCULATION OF A PERSON DURING ASSISTED BREATHING BY MEANS OF A RESPIRATOR

(75) Inventors: Marc Wysocki, Chevreves (FR); Josef Brunner, Chur (CH); Ricardo Lopez Gasco, Wadenswil (CH); Dominik Novotni, Chur (CH); Thomas Laubscher, Rhazuns (CH); Gion Durisch, Domat/Ems (CH)

(73) Assignee: HAMILTON MEDICAL AG (CH)

( * ) Notice: Subject to any disclaimer, the term of this patent is extended or adjusted under 35 U.S.C. 154(b) by 1335 days.

(21) Appl. No.: 12/989,475

(22) PCT Filed: Apr. 23, 2009

(86) PCT No.: PCT/CH2009/000132
§ 371 (c)(1),
(2), (4) Date: Jan. 10, 2011

(87) PCT Pub. No.: WO2009/129641
PCT Pub. Date: Oct. 29, 2009

(65) Prior Publication Data
US 2011/0257549 A1 Oct. 20, 2011

(30) Foreign Application Priority Data
Apr. 24, 2008 (CH) .......................... 650/08

(51) Int. Cl.
*A61B 5/02* (2006.01)
*A61B 5/087* (2006.01)
*A61M 16/00* (2006.01)

(52) U.S. Cl.
CPC .............. *A61B 5/02028* (2013.01); *A61B 5/087* (2013.01); *A61M 16/0051* (2013.01); *A61M 2016/0027* (2013.01); *A61M 2016/0036* (2013.01); *A61M 2230/205* (2013.01)

(58) Field of Classification Search
CPC ........ A61B 5/02; A61B 5/02028; A61B 5/08; A61B 5/087–5/0878; A61M 2016/00–2016/1035
USPC .................................................. 600/529–543
See application file for complete search history.

(56) References Cited

U.S. PATENT DOCUMENTS

2003/0167010 A1* 9/2003 Pinsky .......................... 600/485
2004/0249297 A1* 12/2004 Pfeiffer et al. ................. 600/526

(Continued)

FOREIGN PATENT DOCUMENTS

| EP | 1 434 141 | 6/2004 |
| EP | 1 813 187 | 8/2007 |

(Continued)

OTHER PUBLICATIONS

Murray et al. "The peripheral pulse wave: information overlooked." J Clin Monit. Sep. 1996;12(5):365-77.*

(Continued)

*Primary Examiner* — Navin Natnithithadha
*Assistant Examiner* — Meredith Weare
(74) *Attorney, Agent, or Firm* — Morriss O'Bryant Compagni, PC

(57) ABSTRACT

The invention relates to an apparatus with sensing means suitable for sensing the inspiratory phase and the expiratory phase of each respiratory cycle of a respirated person from in each case at least one minimum and maximum amplitude of a circulation value within a single respiratory cycle, and with a computing device for calculating a variation of the amplitudes of the circulation value occurring within a said respiratory cycle. It is distinguished by the fact that the computing device is set up to assign each amplitude of the circulation value either to the inspiratory phase or to the expiratory phase and to determine the one extreme amplitude of the circulation value from the amplitudes assigned to the inspiratory phase and the other extreme amplitude of the circulation value from the amplitudes assigned to the expiratory phase, and to ascertain from the amplitude variation between the extreme amplitudes in the two phases of the respiratory cycle whether the haemodynamic stress caused by the assisted breathing is too high.

29 Claims, 3 Drawing Sheets

(56) References Cited

U.S. PATENT DOCUMENTS

| | | | |
|---|---|---|---|
| 2007/0027375 A1* | 2/2007 | Melker et al. | 600/340 |
| 2008/0045845 A1* | 2/2008 | Pfeiffer et al. | 600/485 |
| 2008/0064965 A1* | 3/2008 | Jay et al. | 600/484 |
| 2012/0078069 A1* | 3/2012 | Melker | 600/340 |
| 2012/0179051 A1* | 7/2012 | Pfeiffer et al. | 600/484 |
| 2013/0204104 A1* | 8/2013 | Michard et al. | 600/323 |

FOREIGN PATENT DOCUMENTS

| | | |
|---|---|---|
| EP | 1 870 035 | 12/2007 |
| WO | WO 03/077854 | 9/2003 |
| WO | WO 2005/065540 | 7/2005 |

OTHER PUBLICATIONS

Michard, Frederic. "Changes in Arterial Pressure during Mechanical Ventilation." Anaesthesiology 2005, vol. 103:419-428.

Cannesson, Maxime et al. "Does the Pleth Variability Index Indicate the Respiratory-Induced Variation in the Plethysmogram and Arterial Pressure Waveforms?" Anesthesia & Analgesia vol. 106, No. 4, Apr. 2008, pp. 1190-1194.

* cited by examiner

APPARATUS FOR ASSESSING THE STRESS ON THE CIRCULATION OF A PERSON DURING ASSISTED BREATHING BY MEANS OF A RESPIRATOR

CROSS-REFERENCE TO RELATED APPLICATIONS

This application claims priority to PCT Patent Application No. PCT/CH2009/000132 filed on Apr. 23, 2009 and Swiss Patent Application No. 650/08 filed on Apr. 24, 2008, the entirety of each of which is incorporated by reference.

FIELD OF THE INVENTION

The invention relates to an apparatus for assessing the stress on the circulation of a person during assisted breathing.

STATE OF THE ART

A device for assessing the haemodynamic state of a mechanically ventilated patient is known from EP-A 1 813 187. This is set up to provide a respiratory variation diagram of a haemodynamic variable and allows the values of a haemodynamic parameter to be deduced for each mechanical respiratory cycle, as well as evaluation of an assessment of the suitability of these deduced values for haemodynamic analysis on the basis of the respiratory variation diagram. The aim of this analysis is to be able to assess the reaction of the patient to a fluid therapy.

Unsuitable values occur for example if the patient suffers from cardiac arrhythmia or if the patient has irregular breathing patterns, i.e. an irregular respiratory frequency or an irregular tidal volume.

The suitability of a value is assessed on the basis of an arrhythmia. This is determined by recording the time intervals between the pulse-to-pulse peaks of the haemodynamic variables, or by means of ECG. A time interval in which the value of the haemodynamic parameter is suitable has a maximum of a pre-determined difference from a mean time interval. In the case of time intervals with a greater difference the value of the haemodynamic parameter is excluded from analysis.

The suitability of a value is also assessed on the basis of determination of an irregular breathing pattern. This is determined on the basis of the pattern of the values of the haemodynamic parameter. The values of the haemodynamic parameter, which are assigned to the mechanical respiratory cycle pattern, are excluded from analysis if the differences in the respiratory cycle exceed a predetermined value.

The haemodynamic parameter is the variation of the normalized arterial blood pressure PP. According to this document and on the application date of the known teaching the variation PPV in the normalized arterial blood pressure PPn provides information about a reaction of the cardiac volume to fluid therapy. This variation PPV is determined according to formula:

$$PPV = 2\frac{PPn\ \max - PPn\ \min}{PPn\ \max + PPn\ \min}.$$

The described device can be directly connected to a ventilator. The ventilator then sends tidal volumes and/or respiratory tract pressure and/or respiratory tract flow measuring signals to the device. The device can use the pulse-oximetry plethysmographic wave form as the haemodynamic variable and the variation therein as the haemodynamic parameter. At the time the relevant research results were published the inventor had not documented whether these pulse-oximetry signals were significant ("Changes in Arterial Pressure during Mechanical Ventilation" Frederic Michard, Anaesthesiology 2005, vol. 103:419-428).

From the publication "Does the Pleth Variability Index Indicate the Respiratory-Induced Variation in the Plethysmogram and Arterial Pressure Waveforms?" Maxime Cannesson et al., in ANESTHESIA & ANALGESIA vol. 106, No. 4, April 2008, on pages 1190-1194 a person skilled in the art knows that the variation of the amplitudes of a plethysmogram is calculated from the minimum and maximum amplitudes which are measured within a given time period, namely a respiratory cycle.

It is therefore an advantage of the invention to provide an apparatus for assessing the haemodynamic stress on a mechanically ventilated person in which correlation of the assessment with the actual stress is high. In particular, the present invention provides an apparatus that can reliably determine the haemodynamic stress on the person by non-invasive means.

SUMMARY OF THE INVENTION

The advantages of the present invention are achieved by an apparatus for assessing the stress on the circulation of a person during assisted breathing comprising a sensor configured for sensing a inspiratory phase and an expiratory phase of a respiratory cycle of a respirated person and for sensing at least one minimum and at least one maximum amplitude of a circulation value within the respiratory cycle, a computing device for calculating a variation of the at least one minimum and at least one maximum amplitudes of the circulation value occurring within the respiratory cycle, to assign each amplitude of the circulation value either to the inspiratory phase or to the expiratory phase, to determine a first extreme amplitude of the circulation value from the amplitudes assigned to the inspiratory phase and a second extreme amplitude of the circulation value from the amplitudes assigned to the expiratory phase, and to determine from the variation between the first and second extreme amplitudes in the inspiratory and expiratory phases of the respiratory cycle whether a haemodynamic stress caused by assisted breathing is too high.

The apparatus according to the invention can non-invasively and continuously assess the stress on the circulation of a mechanically ventilated person. For this purpose the apparatus has devices for determining the respiratory cycle and the variation of a circulation value, which is representative of the circulation, within the respiratory cycle. This continuously calculated variation is used as a measure of the stress on the circulation, which can be constantly displayed, and can be used as monitoring of the circulation of a mechanically ventilated person. Furthermore, this variation may be used to control the automatic apparatus settings changes and therefore to constantly adjust the settings to the patient.

An apparatus according to the invention comprises sensing means suitable for sensing the respiratory cycles of a person, in particular the inspiratory phase and the expiratory phase of each respiratory cycle, and are suitable for sensing in each case at least one minimum (ZAmin) and one maximum (ZAmax) amplitude of a circulation value (Z) within a single respiratory cycle. An apparatus according to the invention also has a computing device for calculating a variation (ZAV) in the amplitudes of the circulation value occurring within said respiratory cycle.

The computing device is configured to assign each amplitude of the circulation value to the inspiratory phase or to the expiratory phase. It is also configured to determine one extreme, for example the maximum, amplitude of the circulation value from the amplitudes assigned to the inspiratory phase and the other extreme, for example the minimum, amplitude of the circulation value from the amplitudes assigned to the expiratory phase. It is also configured to determine from the amplitude variation between the extreme amplitudes in the two phases of the respiratory cycle whether the haemodynamic stress caused by the assisted breathing is too high.

In one embodiment of the invention, the circulation value is a pulse-oximetry plethysmographic measured value POP. If, however, an invasive measurement is accepted, or required, the circulation value may also be determined from this measurement. It has been found, however, that, because of the inventive choice of maxima and minima of the amplitudes of the circulation value, the relevance of the plethysmographic wave form of the pulse oximeter signal could also be increased.

Previously, a person skilled in the art has assumed that a maximum value of the amplitude of a circulation value, for example of the arterial blood pressure, in respirated patients is always within the inspiratory phase and the minimum value of the amplitude is always within the expiratory phase (cf. notes related to FIG. 5 of "Using heart-lung interactions to assess fluid responsiveness during mechanical ventilation", Crit Care 2000, 4:282-289, 1 Sep. 2000). The correlation of the pulse-oximetry plethysmographic wave form with the cardiac output volume was observed in tests by the inventor on mechanically respirated living organisms. It has been found that the above-stated assumption is not always correct. In the case of mechanically respirated persons greater amplitudes of the circulation value can occur within the expiratory phase than within the inspiratory phase (FIG. 1).

A higher correlation between the variation of the amplitude of the circulation value and the cardiac output volume could be achieved by eliciting the maximum amplitudes within only the inspiratory phase and the minimum amplitudes within only the expiratory phase. The assignment of each maximum or minimum amplitude to an inspiratory or expiratory phase tallies with the change in the pressure conditions within the chest between the two phases of the breath. As a result of this assignment, a filtering is incorporated which artificially helps, for example due to the movement of the patient, to find situations that occur where the minimum and maximum amplitudes take place in the same respiratory phase. As such situations can occur very frequently in practice, the calculation based on this assignment is much more robust compared with a calculation which allows the minimum and maximum amplitudes to be associated with the same respiratory phase.

The computing unit advantageously determines not just one of the two possible extreme amplitudes of each respiratory phase, but both. In an advantageous embodiment the computing unit is therefore configured in such a way that it determines a minimum and a maximum amplitude respectively in both the expiratory phase and the inspiratory phase. It is also set up in such a way that it calculates both amplitude variations per respiratory cycle from these four values and, more precisely, between the minimum amplitude in the inspiratory phase and the maximum amplitude in the expiratory phase and between the maximum amplitude in the inspiratory phase and the minimum amplitude in the expiratory phase.

The computing unit is in this case expediently configured in such way that of the two calculated amplitude variations in the respiratory cycle it takes the larger one as the one that is significant for the haemodynamic stress. In the case of an actively breathing patient it may be the case that the variation turns out to be exactly the opposite of that in the case of a passive patient (see FIG. 2). The larger of the two variations is then the variation between the maximum amplitude in the expiratory phase and the minimum amplitude in the inspiratory phase.

An apparatus of this kind would then be constructed to determine the maximum and minimum amplitudes of the circulation value during breathing from the amplitudes assigned to the expiratory phase and the maximum and minimum amplitudes of the circulation value from the amplitudes assigned to the inspiratory phase, and to calculate a value ($\alpha$) from the variance in these amplitudes which is representative of the haemodynamic stress on the person. An apparatus of this kind that processes the plethysmographic wave form of the pulse oximeter signal is unique as it allows the haemodynamic state of actively breathing and passively respirated patients to be assessed.

The computing unit is configured in such a way that during respiration the value ($\alpha$) is continuously and non-invasively calculated and displayed. No external stimulus, manoeuvre or change in normal respiration is required to determine the stress on the patient's circulation by means of $\alpha$.

In connection with mechanically respirated persons it is primarily of interest to keep the effect of respiration on the circulation under control. An apparatus is therefore provided in which the computing device is configured to use the variation of the amplitudes of the circulation values of a respiratory cycle as a basis for determining an adjusted end-expiratory pressure PEEP and to pass this PEEP that is to be used to mechanical respiration. If the apparatus is capable of inferring the effect of the cardiac output volume due to the given PEEP on the basis of the change in the plethysmographic pulse oximeter signal, the effect of respiration may be optimised by optimising the PEEP. For this purpose limit values for the maximum admissible variation of the amplitude of the circulation value are advantageously fixed and used by the computing unit. These limit values may be fixed so as to be age-dependent, constitution-dependent and/or dependent on the physical condition of the lungs (for example compliance) and the blood vessels (for example arteriosclerosis).

The computing unit is expediently constructed in such a way that it decides on the basis of the variation of the amplitudes of the circulation value of a respiratory cycle and by comparison with stored limit values whether the PEEP can be increased or must be reduced.

The PEEP decision is advantageously based on an averaged variation of the amplitudes ZA of the circulation value Z of successive respiratory cycles taken into account in the PEEP decision. An averaging is the formation of the median ZAVmed from a plurality of determined variations ZAV. The number of considered respiratory cycles that is used is stored in the computing unit but can be changed.

The variation ZAV in the amplitude ZA of the circulation value Z of a respiratory cycle to be used for assessing the haemodynamic stress or determining an appropriate PEEP is expediently normalized, and generalized in particular according to formula:

$$ZAV1 = 2\frac{ZA\ \text{insp-max} - ZA\ \text{exp-min}}{ZA\ \text{insp-max} + ZA\ \text{exp-min}} \quad \text{(Equation 1a)}$$

or $$ZAV2 = 2\frac{ZA\ \text{insp-min} - ZA\ \text{exp-max}}{ZA\ \text{insp-min} + ZA\ \text{exp-max}} \quad \text{(Equation 1b)}$$

or based specifically on the pulse oximetry signal according to formula:

$$POPV1 = 2\frac{POP\ \text{insp-max} - POP\ \text{exp-min}}{POP\ \text{insp-max} + POP\ \text{exp-min}} \quad \text{(Equation 2a)}$$

or $$POPV2 = 2\frac{POP\ \text{insp-min} - POP\ \text{exp-max}}{POP\ \text{insp-min} + POP\ \text{exp-max}} \quad \text{(Equation 2b)}$$

A percentage may also be used by multiplying the above-shown value by 100.

The larger of the amounts is taken from the two values ZAV1 and ZAV2 or POPV1 and POPV2. The higher value is taken as being relevant for the statement about whether the haemodynamic stress caused by respiration is acceptable or too high. For this purpose the higher value is compared with a constant k dependent on PEEP. If the value is higher than k, when the sign is taken into account, the haemodynamic stress is too high. If this value is lower than k or equal to k, when the sign is taken into account, the stress is within the bounds of what is reasonable. One embodiment of the invention also comprises display means. These show the amplitude variation, or they show the deduction from the amplitude variation, which indicates whether the haemodynamic stress caused by respiration is too high for the person or not. The calculated amplitude variation, or deduction from the amplitude variation, can be compared with a stored limit value and if this limit value is exceeded this can be displayed as a visual or acoustic signal. As a result the medical staff, for example, is kept constantly informed about the haemodynamic state of the patient. The medical staff is therefore warned in good time in the event of an unfavourable change in the circulation. The display means can optionally indicate a trend of one of these variables. The display means may also display a plurality of the stated values.

The apparatus according to the invention may be a respirator. In this case the sensing means for sensing the respiratory cycle and the respiratory phases are integrated in the respirator. The respirator advantageously comprises a pulse oximeter as a sensor for determining the circulation value.

The apparatus can, however, also be a monitoring device without a respiration function. It then comprises a monitoring device, a pulse oximeter and sensing means, connected to the monitoring device, for sensing the respiratory cycle and the respiratory phases.

The situation can occur where there are insufficient pulses in the inspiratory or expiratory phase for minimum and maximum amplitudes to be determined. One possibility of reacting to the illustrated situation in order to obtain usable results consists in eliciting only one maximum value and one minimum value over a plurality of inspiratory phases and a plurality of expiratory phases and to use this variation within a plurality of respiratory cycles for the assessment to determine the haemodynamic stress on the patient. In particular, respiratory phases without amplitude are not taken into account. For this purpose it is necessary for the computing unit to assign the amplitudes over a plurality of respiratory cycles to the inspiratory phases or the expiratory phases respectively and to determine one extreme value of the amplitudes from the amplitudes assigned to the inspiratory phases and the other extreme value from the amplitudes assigned to the expiratory phases of this plurality of respiratory cycles.

The invention also relates to a method. The method incorporates the following steps:
sensing the respiratory cycles of a person and the inspiratory phase and the expiratory phase of each respiratory cycle,
sensing in each case at least one minimum and one maximum amplitude of a circulation value within a single respiratory cycle,
calculating a variation of the amplitudes of the circulation value occurring within said respiratory cycle and which is representative of a haemodynamic state of the person.

The method further includes the step of assignment of each amplitude of the circulation value to the inspiratory phase or the expiratory phase, and subsequent determination of the maximum and minimum amplitudes of the circulation value within a specific respiratory phase. In the case of a person respirated with a respirator pressure, the maximum amplitude of the circulation value is determined from the amplitudes assigned to the inspiratory phase and the minimum amplitude of the circulation value is determined from amplitudes assigned to the expiratory phase. In the case of an actively breathing person, on the other hand, the maximum amplitude of the circulation value is conversely determined from the amplitudes assigned to the expiratory phase and the minimum amplitude of the circulation value is determined from the amplitudes assigned to the inspiratory phase.

A further embodiment of the invention consists of the use of the variation of the amplitudes of the circulation values of a respiratory cycle as a basis for determining an upper limit of the end-expiratory pressure PEEP for respiration of the person.

BRIEF DESCRIPTION OF THE DRAWINGS

The invention will be described in detail hereinafter with reference to the figures, in which, schematically.

DETAILED DESCRIPTION OF THE ILLUSTRATED EMBODIMENTS

Figure 1:
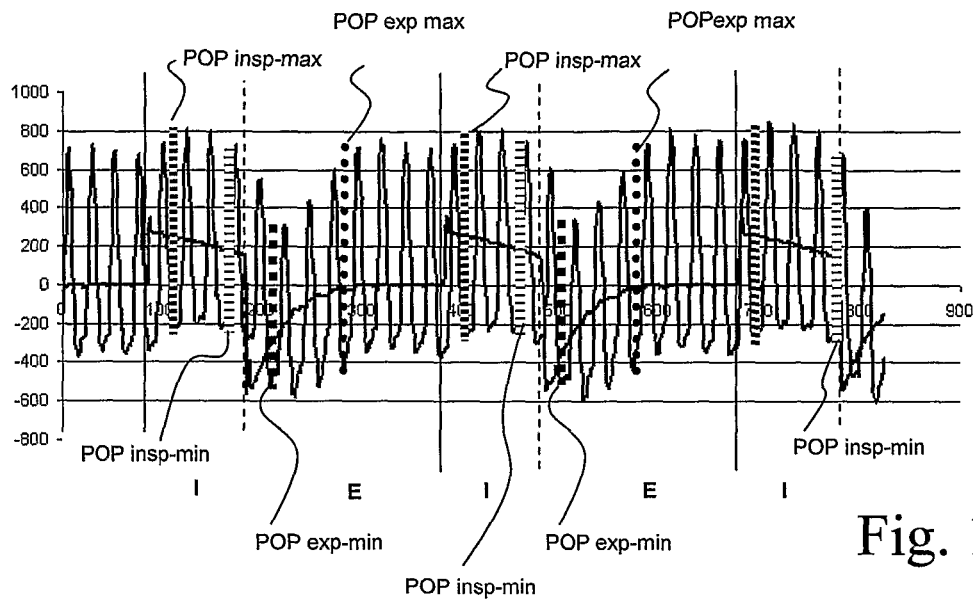
FIG. 1 shows a pulse oximeter plethysmogram with correlated flow chart of a mechanically respirated person.

The respiratory cycles of a person mechanically respirated by means of positive respiration pressure, diagrammatically shown in FIG. 1, are illustrated by the flow curve of the respiratory gas. A solid line marks the beginning of the inspiratory phase and a broken line the beginning of the expiratory phase. The plethysmogram of a pulse oximeter is laid over this flow curve. The plethysmographic wave form correlates with the flow curve. In a similar manner it also correlates with a pressure curve (not shown here), be this based on the pressure of the respiratory gas or an internal pressure of the thorax.

The plethysmogram illustrates a wave form with superimposed waves. One of the waves shows the pulse frequency, the other the respiratory frequency. The maxima of the plethysmogram in the pulse frequency increase in the respiratory frequency during the course of the expiratory phase and at the start of the inspiratory phase and decrease again during the course of the inspiratory phase and at the start of the expiratory phase. This increase and decrease does not occur simultaneously in the case of the minima, however. The amplitude between the minima and maxima occurring in the pulse frequency is not constant but dependent on the respiration pressure, in particular on the PEEP, and on the haemodynamic stability of the respirated person. The variation of amplitudes is greater in the case of haemodynamically unstable persons than in the case of haemodynamically stable persons. With a higher PEEP the variation of amplitudes is greater than with a lower PEEP. Similar to in the case of the amplitudes of the arterial blood pressure, where a variation of amplitude provides information about the sensitivity of the patient to a fluid therapy, this variation of amplitude in the plethysmogram provides information about the haemodynamic stress on the patient due to mechanical respiration.

It has been found that, contrary to the previous assumption, the maximum amplitude within a mechanically respirated respiratory cycle is not always in the inspiratory phase and the minimum amplitude can also sometimes be in the inspiratory phase. In FIG. 1 both the absolute maximum amplitude (POP exp-max) and the absolute minimum amplitude (POP exp-min) for example lie within the expiratory phase. According to the invention it is not both absolute values that are used to create the variation formed for the haemodynamic assessment of the person. Instead the maximum amplitude within the inspiratory POP insp-max and the minimum amplitude within the expiration POP-exp-min, which in this case is identical to the absolute minimum amplitude, are used. The use of the values based on the individual phases produces a greater correlation between the variation of the amplitudes of the plethysmogram and the cardiac output volume than the use of the absolute maximum and minimum amplitudes alone.

In the case shown in FIG. 1 the instantaneous, incomplete respiratory cycle is shown on the right. The POPV is calculated at the end of a respiratory cycle, so at the illustrated instant the POPV calculation exists at least for the penultimate respiratory cycle shown on the left.

Figure 2:
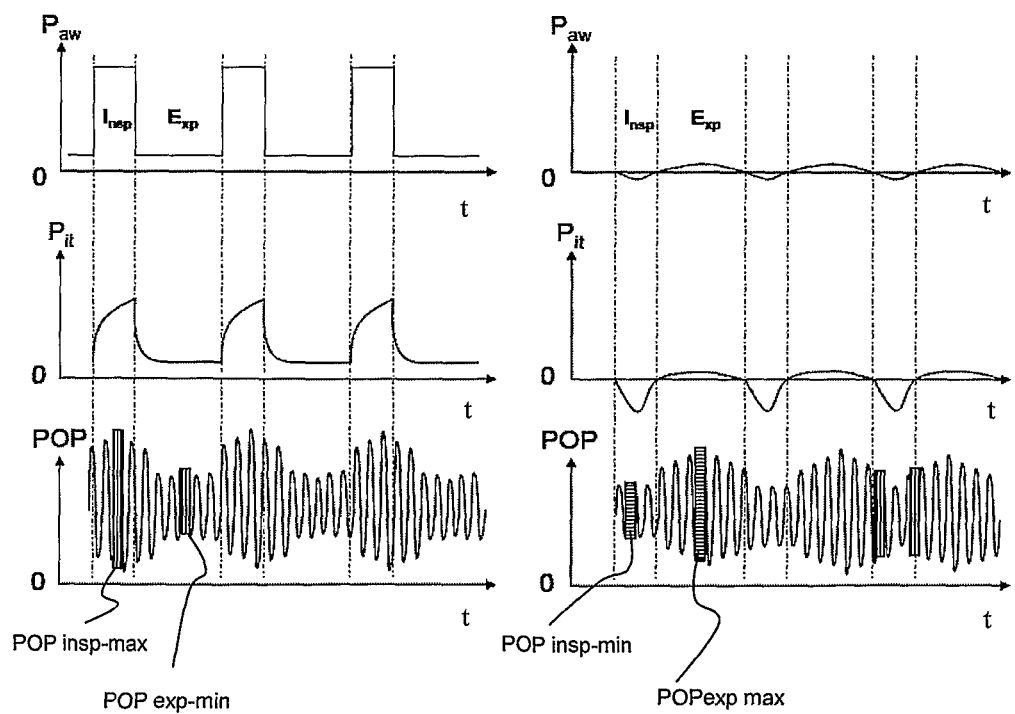
FIG. 2 shows a comparison of pressure graphs and plethysmogram in the case of a mechanically respirated patient and in the case of an actively breathing haemodynamically unstable patient.

FIG. 2 shows six graphs, namely three schematic graphs, one above the other respectively, relating to a mechanically respirated patient on the left-hand side and three schematic graphs relating to a spontaneously and actively breathing person on the right-hand side. The top graphs show the respiratory tract pressure Paw over three respiratory cycles, the middle graphs schematically show a thorax internal pressure Pit, for example the pleural pressure, over these three respiratory cycles. The bottom graphs show the pulse-oximetric plethysmogram POP over the same respiratory cycles. The three curves in the associated graphs are correlated in terms of time. The limits between the inspiratory phase Insp and expiratory phase Exp are denoted by broken lines which extend across all three graphs.

The graphs illustrating POP show the plethysmographic wave form. Therein the maximum amplitudes POP insp-max within the inspiratory phase and the minimum amplitudes POP exp-min within the expiratory phase are denoted by vertically hatched stripes. In the case of a mechanically respirated and haemodynamically unstable person the difference in POP insp-max minus POP exp-min is high and positive. In the case of an actively breathing and haemodynamically unstable person values around zero are produced, however. If, on the other hand, the minimum amplitude POP insp-min is determined in the inspiratory phase and the maximum amplitude POP exp-max in the expiratory phase, a relatively high, but negative, value is again produced from POP insp-min minus POP exp-max. These last two amplitudes are denoted by horizontally hatched stripes. In the inventors' opinion the greater variation of that described above is the more significant, irrespective of whether the person is active or passive.

Figure 3:
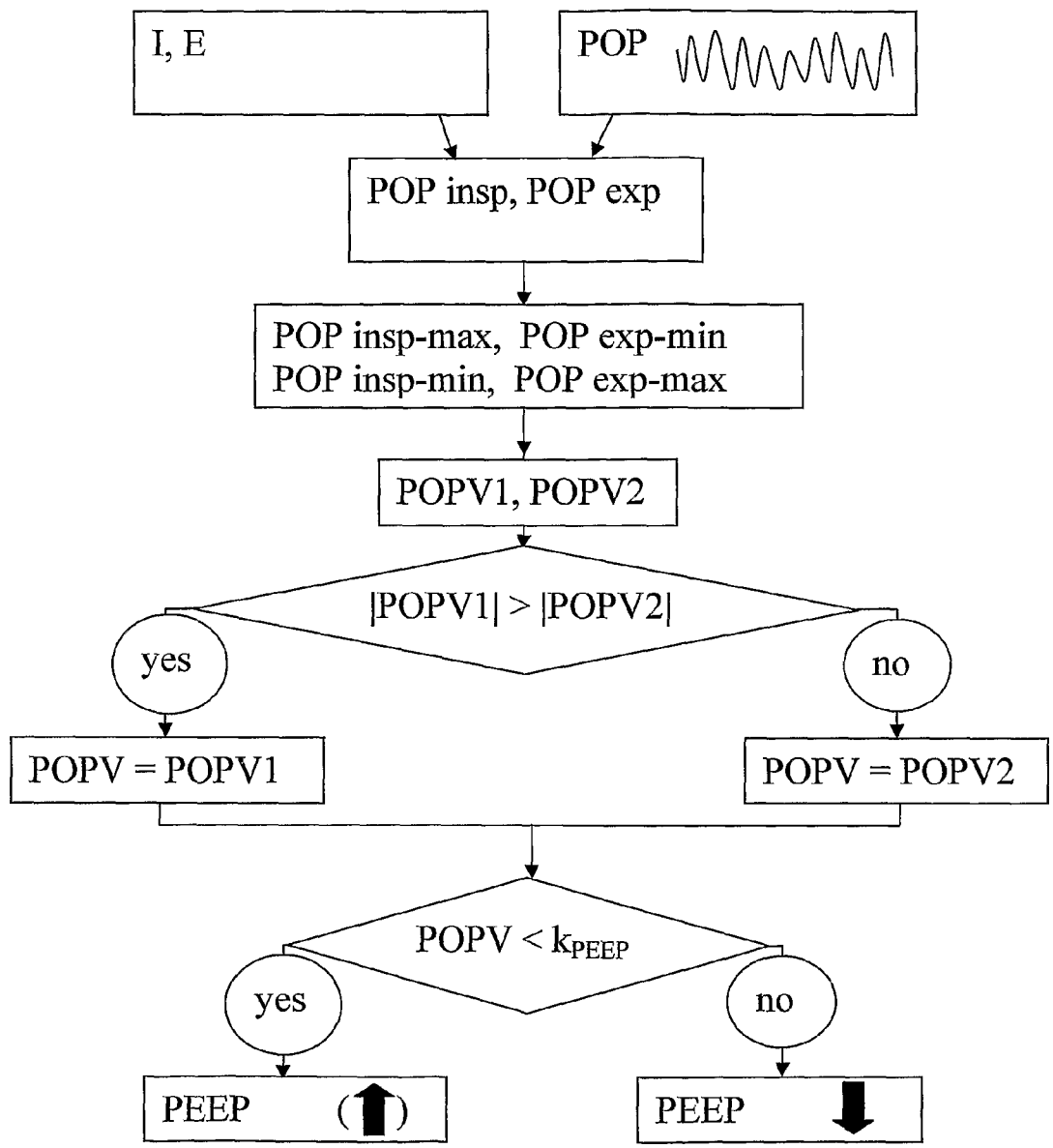
FIG. 3 shows a flow chart of the method.

The flow chart shown in FIG. 3 illustrates the progress of the decision method executed by the computing unit of the apparatus. In each respiratory cycle firstly the inspiratory phase I and then the expiratory phase E is detected. The plethysmogram is simultaneously shown. In a simple embodiment the maximum amplitude POP insp-max within the inspiratory phase I and the minimum amplitude POP exp-min within the expiratory phase E is then determined and from this, for example according to equation 2a, POPV, i.e. the variation of these amplitudes is determined. This variation is then compared with a PEEP-dependent constant k. If POPV is less than this constant k representing a limit value for POPV, the PEEP used may be increased. If POPV is greater than or equal to k, the PEEP must be reduced. It is also possible to determine a region around k within which PEEP is left.

In one embodiment, both the maximum and minimum amplitudes are determined in each phase and in each case the maximum or minimum amplitude in the inspiratory phase minus the minimum or maximum amplitude in the expiratory phase is calculated. The greater variation of amplitude is then determined and the sign of the greater amplitude taken into account. The procedure is then as described above, with the positive or negative value of the greater variation of amplitude being used. The comparison of the variation of amplitude with the constant k dependent on the currently adjusted PEEP indicates whether the PEEP may be increased if required (arrow set in brackets) or whether it must be decreased. A negative variation of amplitude, in the case of an actively breathing person, is not a reason to reduce PEEP, however, as this value is always less than k.

Figure 4:
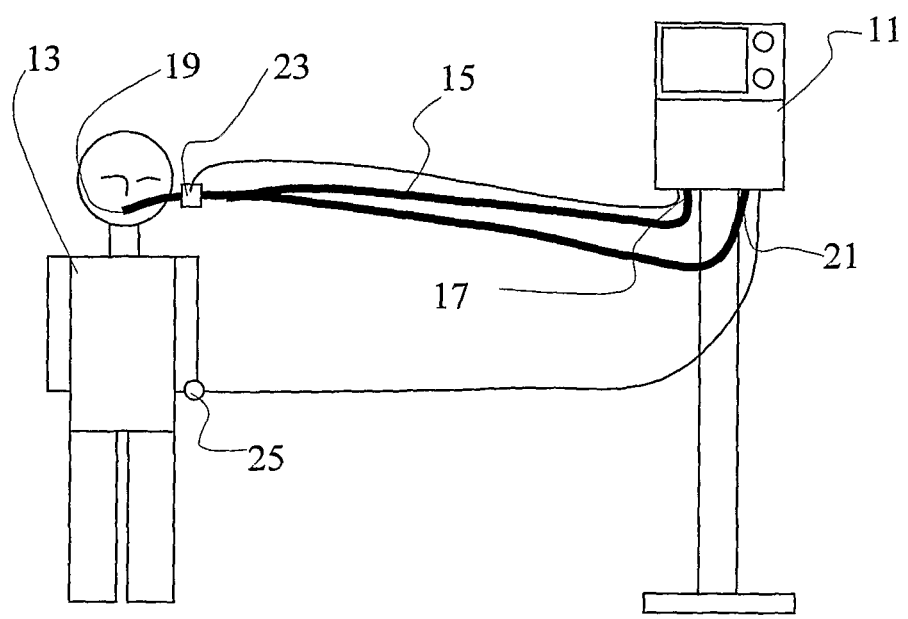
FIG. 4 shows a person connected to a respirator according to the invention.

The respirator 11 shown in FIG. 4 is connected to a respirated person 13. A y-shaped respiratory tube 15 connects the pressure side of the respirator 11, or the output 17 downstream of the inspiratory valve, to the mouthpiece 19 on the one hand, and on the other hand, the mouthpiece 19 to the connector 21 to the expiratory valve in the respirator 11. Valves and pressure and/or flow sensors, for example 23, are arranged in the respirator and in the respiratory tube 15. These provide information about inspiratory phases and expiratory phases and therewith about the respiratory cycles. The respirator provides the pressures and volumes required for respiration in rhythm with the respiratory cycles.

A pulse oximeter 25 is arranged on the hand of the patient 13 and is connected to the respirator 11. The signals from the oximeter are correlated in terms of time by the computer of the respirator 11 with the information about the respiratory phases and the frequency and amplitudes thereof are analysed. Usable minimum and maximum amplitudes are determined from the two respiratory phases and the variation of amplitude POPV suitable for subsequent use is determined according to equations 2a/2b and a comparison of the two variations in amplitude obtained. A decision is made on the basis of the POPV obtained and a limit value k as to whether the existing PEEP may be increased, is at a maximum value or must be reduced. This decision is optionally also based on the values, or individual patient-specific values, which are captured in the respirator, or the limit value k is optionally fixed in accordance with these patient-specific values.

If on the basis of the plethysmographic signal of the pulse oximeter and the respiratory phases it is accordingly found that the cardiac output volume is too severely affected by respiration the PEEP is reduced until the wave form of the plethysmogram no longer requires it. If the patient is haemodynamically unstable, however, the PEEP influences the plethysmographic wave form only slightly and the PEEP can be increased above the currently applied PEEP, if this is desired owing to considerations relating to respiration technology.

Known processes and known devices may be used in the case of the PEEP decision, triggering of the respiratory cycles and detecting the effectiveness of ventilation and the O2 supply regardless of inventive analysis of the haemodynamic stress due to the changing pressures inside the thorax.

The invention claimed is:

1. An apparatus for assessing the stress on the circulation of a person during respirator-assisted breathing, comprising:
 a sensor configured for sensing and generating signals representing an inspiratory phase and an expiratory phase of a respiratory cycle of a respirated person, the signals comprising at least one minimum and at least one maximum amplitude of a circulation value within the respiratory cycle;
 a computing device adapted to communicate with a respirator and configured to:
  receive the signals;
  calculate a variation of the at least one minimum and at least one maximum amplitudes of the circulation value occurring within the respiratory cycle;
  assign each amplitude of the circulation value either to the inspiratory phase or to the expiratory phase;
  determine a first extreme amplitude of the circulation value from the amplitudes assigned to the inspiratory phase and a second extreme amplitude of the circulation value from the amplitudes assigned to the expiratory phase;
  determine from the variation between the first and second extreme amplitudes in the inspiratory and expiratory phases of the respiratory cycle whether a haemodynamic stress caused by assisted breathing is too high; and
 if the haemodynamic stress caused by assisted breathing is determined by the computing device to be too high, determine and communicate an adjusted end-expiratory pressure PEEP of mechanical respiration for a respirator of the mechanically respirated person to the respirator to adjust an end-expiratory pressure PEEP setting of the respirator accordingly.

2. The apparatus according to claim 1, wherein the computing device is configured to determine a maximum and a minimum amplitude for each of the inspiratory phase and the expiratory phase of the respiratory cycle, and to determine both amplitude variations between the maximum amplitude in one phase and the minimum amplitude in the other phase.

3. The apparatus according to claim 2, wherein the computing device is configured to utilize the larger of the determined amplitude variations as a relevant value for determining the haemodynamic stress on the person.

4. The apparatus according to claim 1, further comprising a display for displaying at least one of the amplitude variation, the determination from the amplitude variation that indicates whether the haemodynamic stress caused by assisted breathing is too high for the person, and a trend of at least one of the amplitude variation and the determination of the amplitude variation.

5. The apparatus according to claim 1, wherein the computing device is configured to determine on a basis of the variation of the amplitudes of the circulation values of a respiratory cycle whether an end-expiratory pressure PEEP of the respirator may be increased or must be reduced.

6. The apparatus according to claim 5, wherein the computing device calculates a difference in variation between a minimum or maximum amplitude in the inspiratory phase and a minimum or maximum amplitude in the expiratory phase and determines which difference constitutes a larger variation of the amplitudes of the circulation value and whether the larger variation is positive or negative to determine whether the end-expiratory pressure PEEP of the respirator may be increased or must be reduced.

7. The apparatus according to claim 6, wherein the PEEP decision is based on a median of a plurality of variations of the amplitudes of the circulation value of successive respiratory cycles taken into account in the PEEP decision.

8. The apparatus according to claim 7, wherein a variation ZAV in an amplitude ZA of a circulation value Z of a respiratory cycle is normalized according to a formula of one of:

$$ZAV1 = 2\frac{ZA\ \text{insp-max} - ZA\ \text{exp-min}}{ZA\ \text{insp-max} + ZA\ \text{exp-min}}$$

or $$ZAV2 = 2\frac{ZA\ \text{insp-min} - ZA\ \text{exp-max}}{ZA\ \text{insp-min} + ZA\ \text{exp-max}}$$

whereby ZA insp-max is the maximum amplitude of a circulation value within the inspiratory phase, ZA exp-min is the minimum amplitude of a circulation value within the expiratory phase, ZA insp-min is the minimum amplitude of a circulation value within the inspiratory phase, and ZA exp-max is the maximum amplitude of a circulation value within the expiratory phase.

9. The apparatus according to claim 8, wherein the circulation value Z is a pulse-oximetry plethysmographic measured value POP.

10. The apparatus according to claim 1 wherein the sensor is connected to the respirator.

11. The apparatus according to claim 10, further comprising a pulse oximeter also connected to the respirator.

12. The apparatus according to claim 11, wherein the computing device is configured to determine only one maximum and one minimum value of the amplitudes over a plurality of inspiratory phases and expiratory phases and to use the variation of the amplitudes within the plurality of inspiratory phases and expiratory phases for evaluation.

13. The apparatus according to claim 1, wherein the computing device is configure to assign the amplitudes from a plurality of respiratory cycles to the inspiratory phases or the expiratory phases and to determine one extreme amplitude of the circulation value from the amplitudes assigned to the plurality of inspiratory phases and the other extreme amplitude of the circulation value from the amplitudes assigned to the plurality of expiratory phases.

14. The apparatus according to claim 1, further comprising a monitoring device and a pulse oximeter connected thereto for sensing the respiratory phases.

15. An apparatus for assessing the stress on the circulation of a person during assisted breathing, comprising:
 a sensing device configured for sensing and generating sensing device signals representing an inspiratory phase and an expiratory phase of a respiratory cycle of a mechanically respirated person;

a pulse oximeter for sensing and generating pulse oximeter signals representing at least one minimum and one maximum amplitude of a circulation value within the respiratory cycle; and
a computing device adapted to communicate with a respirator and configured to:
  receive the sensing device signals and the pulse oximeter signals for calculating a variation of the amplitudes of the circulation value occurring within the respiratory cycle;
  specify an first end-expiratory pressure PEEP of mechanical respiration that is to be used,
  use the variation of the amplitudes of the circulation values of the respiratory cycle as a basis for a decision over an increase or reduction in the first end-expiratory pressure PEEP;
  assign each amplitude of the circulation value to the inspiratory phase or the expiratory phase;
  determine the maximum amplitude of the circulation value from the amplitudes assigned to the inspiratory phase; and
  determine the minimum amplitude of the circulation value from the amplitudes assigned to the expiratory phase; and
  determine a second end-expiratory pressure PEEP of mechanical respiration for the respirator of the mechanically respirated person and communicate the second end-expiratory pressure PEEP to the respirator to adjust an end-expiratory pressure PEEP setting of the respirator accordingly.

16. A method for assessing the stress on the circulation of a person during assisted breathing, comprising:
  using a sensing device to sense and generate signals representing an inspiratory phase and an expiratory phase of each respiratory cycle of a person and at least one minimum and one maximum amplitude of a circulation value within a single respiratory cycle; and
  using a computing device adapted to communicate with a respirator and to calculate a variation of the amplitudes of the circulation value occurring within the respiratory cycle, to assign each amplitude of the circulation value to the inspiratory phase or the expiratory phase, and to determine one extreme amplitude of the circulation value from the amplitudes assigned to the inspiratory phase and the other extreme amplitude of the circulation value from the amplitudes assigned to the expiratory phase to further determine whether a haemodynamic stress caused by the assisted breathing is too high; and
  if the haemodynamic stress caused by assisted breathing is determined to be too high, determine an adjusted end-expiratory pressure PEEP of mechanical respiration for the respirator of the mechanically respirated person and communicate the adjusted end-expiratory pressure PEEP to the respirator to adjust an end-expiratory pressure PEEP setting of the respirator accordingly.

17. The method according to claim 16, further comprising using the computing device to determine a maximum and a minimum amplitude for each of the inspiratory phase and the expiratory phase of the respiratory cycle, and to determine both amplitude variations between the maximum amplitude in one phase and the minimum amplitude in the other phase.

18. The method according to claim 17, further comprising using the computing device to utilize the larger of the determined amplitude variations as a relevant value for determining the haemodynamic stress on the person.

19. The method according to claim 16, further comprising using the display for displaying at least one of the amplitude variation, the determination from the amplitude variation that indicates whether the haemodynamic stress caused by assisted breathing is too high for the person, or a trend of at least one of the amplitude variation or the determination of the amplitude variation.

20. The method according to claim 16, further comprising using the computing device to determine on a basis of the variation of the amplitudes of the circulation values of a respiratory cycle whether an end-expiratory pressure PEEP of the respirator may be increased or must be reduced.

21. The method according to claim 20, further comprising using the computing device to calculate a difference in variation between a minimum or maximum amplitude in the inspiratory phase and a minimum or maximum amplitude in the expiratory phase and determine which difference constitutes a larger variation of the amplitudes of the circulation value and whether the larger variation is positive or negative to determine whether the end-expiratory pressure PEEP of the respirator may be increased or must be reduced.

22. The method according to claim 21, further comprising basing the PEEP decision on a median of a plurality of variations of the amplitudes of the circulation value of successive respiratory cycles taken into account in the PEEP decision.

23. The method according to claim 22, further comprising using a variation ZAV in an amplitude ZA of a circulation value Z of a respiratory cycle that is normalized according to a formula of one of:

$$ZAV1 = 2\frac{ZA \text{ insp-max} - ZA \text{ exp-min}}{ZA \text{ insp-max} + ZA \text{ exp-min}}$$

or $$ZAV2 = 2\frac{ZA \text{ insp-min} - ZA \text{ exp-max}}{ZA \text{ insp-min} + ZA \text{ exp-max}}$$

whereby ZA insp-max is the maximum amplitude of a circulation value within the inspiratory phase, ZA exp-min is the minimum amplitude of a circulation value within the expiratory phase, ZA insp-min is the minimum amplitude of a circulation value within the inspiratory phase, and ZA exp-max is the maximum amplitude of a circulation value within the expiratory phase.

24. The method according to claim 23, further comprising using a pulse-oximetry plethysmographic measured value POP as the circulation value Z.

25. The method according to claim 16, further comprising connecting the sensor to the respirator.

26. The method according to claim 16, further comprising connecting a pulse oximeter to the respirator.

27. The method according to claim 26, further comprising using the computing device to determine only one maximum and one minimum value of the amplitudes over a plurality of inspiratory phases and expiratory phases and to use the variation of the amplitudes within the plurality of inspiratory phases and expiratory phases for evaluation.

28. The method according to claim 16, further comprising using the computing device to assign the amplitudes from a plurality of respiratory cycles to the inspiratory phases or the expiratory phases and to determine one extreme amplitude of the circulation value from the amplitudes assigned to the plurality of inspiratory phases and the other extreme amplitude of the circulation value from the amplitudes assigned to the plurality of expiratory phases.

29. The method according to claim 16, further comprising using a monitoring device and a pulse oximeter connected thereto for sensing the respiratory phases.

\* \* \* \* \*